US005783194A

United States Patent [19]
Brown et al.

[11] Patent Number: 5,783,194
[45] Date of Patent: Jul. 21, 1998

[54] HOMOGENEOUS ISOLATE OF URABE MUMPS VIRUS AND VACCINES CONTAINING THE ISOLATE

[75] Inventors: Earl G. Brown, Nepean; Kathryn E. Wright; Kenneth D. Dimock, both of Gloucester, all of Canada

[73] Assignee: University of Ottawa, Ottawa, Canada

[21] Appl. No.: 594,295

[22] Filed: Jan. 30, 1996

[51] Int. Cl.[6] .......................... A61K 39/155; C12N 7/00
[52] U.S. Cl. ............................ 424/211.1; 435/235.1; 514/44
[58] Field of Search ................. 424/211.1; 435/235.1; 514/44

[56] References Cited

PUBLICATIONS

Brown et al. Vaccine. vol 9. Nov. 1991, pp. 840–842.

*Primary Examiner*—Ponnathapura Achutamurthy
*Assistant Examiner*—Phuong T. Bui
*Attorney, Agent, or Firm*—Sim & McBurney

[57] ABSTRACT

A new attenuated substantially homogeneous Urabe mumps virus strain characterized by having a codon encoding glutamic acid at amino acid position 335 of the haemagglutinin-neuraminidase (HN) protein is provided. The codon may be GAA resulting in the abolition of an MseI restriction enzyme recognition site in the native virus. The invention also provides a gene encoding the HN (Glu-335) protein. The virus has utility in attenuated mumps vaccines, and as an antigen and immunogen in diagnostic embodiments.

8 Claims, 8 Drawing Sheets

```
               10         20         30         40         50         60         70
                *          *          *          *          *          *          *
URABE   MEPSKLFTMS DNATFAPGPF INAADKKIFR TCFRIILVLSV QAVTLILVIV TLGELVRMIN DQGLSNQLSS
1004    ---------- ---------- ---------- ---------- ---------- ---------- ----------
MIY     ---------- -----V---- ---------- ---------- ---------- ---------- ----------
891     -------I-- -DT--V---- ---------- ---------- ---------- ---------- ----------
RW      -------I-- -----VN--- ---------- ---------- ---------- ---------- ----------
CA      -------I-- -----V---- ---V---G-- ---------- ---------- ---I----I- ----------
KS      -------I-- -----V---- ---V---G-- ---------- ---------- ---I----I- ----------
JL      -------I-- -----V---- ---V---G-- ---------- ---------- ---I------ ----------
SBL     -------I-- ----VV---- ---V---G-- ---------- ---------- ---I------ ----------

80         90        100        110        120        130        140
                *          *          *          *          *          *          *
URABE   IADKIRESAT MLASAVGVMN QVIHGVIVSL PLQIEGNQNQ LLSTLATICT GKKQVSNCST NIPLVNDLRF
1004    ---------- ---------- ---------- ---------- ---------- ---------- ----------
MIY     --T--K---- ---------- ---------- ---------- ---------- S----A---I ----------
891     --T------- ---------- ---------- ---------- ---------- S------I-- ----------
RW      --T----A-- ---------- ---------- ---------- ---------- NRN------- ----------
CA      --T----A-- ---------- ---------- ---------- ---------- NRN------- ----------
KS      --T----A-- ---------- ---------A ---------- ---------- NRN------- ----------
JL      --T----A-- ---------- ---------- ---------- ---------- NRN------- ----------
SBL     --T----A-V ---------- ---------- ---------- ---------- NRN------- ----------
```

FIG.2B

```
              150        160        170        180        190        200        210
               *          *          *          *          *          *          *
URABE   INGINKFIIE DYATHDFSIG HPLNMPSFIP TATSPNGCTR IPSFSLGKTH WCYTHNVINA NCKDHTSSNQ
1004    ---------- ---------- ---------- ---------- ---------- ---------- ----------
MIY     ---------- ---------- ---------- ---------- ---------- ---------- ----------
891     ---------- -------N-- ---------- ----Y----- ---------- ---------- ----------
RW      ---------- ---------- ---------- ---------- ---------- ---------- ----------
CA      ---------- ---------- ---------- ---------- ---------- ---------- ----------
KS      ---------- ---------- ---------- ---------- ---------- ---------- ----------
JL      ---------- ---------- ---------- ---------- ---------- ---------- ----------
SBL     ---------- ------N--- ---------- ---------- ---------- ---------- ----------

220        230        240        250        260        270        280
               *          *          *          *          *          *          *
URABE   YISMGILVQT ASGYPMFKTL KIQYLSDGLN RKSCSIATVP DGCAMYCYVS TQLEIDDYAG SSPPIQKLTL
1004    ---V------ ---------- ---------- ---------- ---------- ---------- ----------
MIY     ---V------ ---------- ---------- ---------- ---------- ---------- ----------
891     ---V------ ---------- ---------- ---------- ---------- ---------- ----------
RW      ---V------ ---------- ---------- ---------- ---------- ---------- ----------
CA      ---V------ ---------- ---------- ---------- ---------- ---------- ----------
KS      ---V------ ---------- ---------- ---------- ---------- ---------- ----------
JL      ---V------ ---------- ---------- ---------- ---------- ---------- ----------
SBL     ---V------ ---------- ---------- ---------- ---------- ------AN-- ----------
```

FIG.2C

```
             290        300        310        320        330        340        350
              *          *          *          *          *          *          *
URABE  LFYNDIVIER TISPIGLEGN WATLVPGVGS GIYFENKLIF PAYGGVLPNS TLGVESAREF FRPVNPYNPC
1004   ---------- ---------- ---------- ---------- ---------- ---K------ ----------
MIY    ----I----- -----S---- ---------- ---------- ---------- -S-K------ ----------
891    ---------- -----S---- ---------- ---------- ---------- ---K------ ----------
RW     ----IK---- -----S---- ---------- ---------- ---------- ---KL----- ----------
CA     ----IK---- -----S---- ---------- ---------- ---------- ---K------ ----------
KS     ----IK---- -----S---- ---------- ---------- ---------- ---K------ ----------
JL     ----I----- -----S---- ---------- ---------- ---------- -R-K------ ----------
SBL    ---------- -----S---- ---------- ---------- ---------- ---K------ ----------

360        370        380        390        400        410        420
              *          *          *          *          *          *          *
URABE  SGPQQDLDQR ALRSYFPSYF SNRRVQSAFL VCAWNQILVT NCELVVPSNN QITMGAEGRV LLINNRLLYY
1004   ---------- ---------- ---------- ---------- ---------- ---------- ----------
MIY    ---T-E---- ---------- ---------- ---------- -----I---- ---------- ----------
891    ---T-E---- ------L--- ---------- ---------- -----I---- ---------- ----------
RW     ---P-E---- ---------- -S-------- ---------- ---------- ---------- ----------
CA     ---P-E---- ---------- -S-------- ---------- ---------- ---------- ----------
KS     ---------- ---------- -S-------- ---------- ---------- ---------- ----------
JL     ---------- ---------- -S-------- ---------- ---------- ---------- ----------
SBL    ---------- ------R--- ---------- ---------- ---------- ---------- ----------
```

FIG.2D

```
              430        440        450        460        470        480        490
               *          *          *          *          *          *          *
URABE  QRSTSWWPYE LLYEISFTFT NSQQSSVMMS WIPTYSFTRP GSGNCSGENV CPTACVSGVY LDPWPLTPYS
1004   ---------- ---------- ---------- ---------- ---------- ---------- ----------
MIY    ----G----- ---------- ---------- ---------- ------P--- ---------- ----------
891    ---------- ---------- ---------- ---------- -------K-- ------I--- ----------
RW     ---------- ---------- ---------S ---------- -------L-- ------V--- ----------
CA     ---------- ---------- ---------- ---------- -------L-- ------V--- ----------
KS     ---------- ---------- ---------- ---------- -------L-K ------V--I ----------
JL     ---------- ---------- ---------- ---------- ---------- ---------- ----------
SBL    ---------- ---------- ---------- ---------- -------K-- ------V--- ----------

500        510        520        530        540        550        560
               *          *          *          *          *          *          *
URABE  HQSGINRNFY FTGALLNSST TRVNPTLYVS AINNLKVLAP YGNQLFASY  TTTTCFQDIG DASVYCVYTM
1004   ---------- ---------- ---------- ---------- ---------T --L------- ----------
MIY    ---------- ---------- ---------- ---------- ---------T --S------- ----------
891    ---------- ---------- ---------- ---------- ---------T ---------- ----------
RW     ---------- ---------- ---------- ---------Q ---------T ---------- ----------
CA     ---------- ---------- ---------- ---------- ---------T ---------- ----------
KS     ---------- ---------- ---------- ---------- ---------- ---------- ----------
JL     ---------- ---------- ---------- ---------- ---------T ---------- ----------
SBL    ---------- ---------- ---------- ---------- ---------- ---------- ----------
```

FIG.2E

```
              *        *        *         *
              570               580
URABE   ELASNIVGEF QILPVLTRLT IT
1004    ---------- ---------- --
MIY     ---------- ---------- --
891     ---------- ---------- --
RW      ---------- ---------- --
CA      ---------- -------A-- --
KS      ---------- -------A-- --
JL      ---------- -------A-- --
SBL     ---------- -------A-- --
```

HOMOGENEOUS ISOLATE OF URABE MUMPS VIRUS AND VACCINES CONTAINING THE ISOLATE

FIELD OF THE INVENTION

The present invention relates to the field of vaccines and is particularly concerned with live mumps vaccine strains.

BACKGROUND OF THE INVENTION

Mumps virus is a member of the genus Paramyxovirus in the family Paramyxoviridae, which also includes Newcastle disease virus and parainfluenza viruses. Mumps virus is an enveloped, negative-strand RNA virus that contains six major structural proteins (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Two surface glycoproteins, the hemagglutinin-neuraminidase (HN) and the fusion protein (F), are responsible for viral absorption and fusion of the virion membrane with the host cell membrane, respectively. Both glycoproteins are required for cell fusion.

Before the introduction of mumps vaccine, mumps was most commonly seen among young school-aged children, with the highest incidence rates being among children 5 to 9 years of age. Infection with mumps virus is established by droplet spread to respiratory mucosa and plasma viremia follows primary replication at this site. Viremic spread throughout the body leads to infection of many organs. Clinical symptoms relating to infection of the parotid gland are most typical but many other organs, such as testes, kidney, pancreas, heart, joints and lung, are commonly affected as well. Half of all clinical infections have evidence of CNS invasion (as CSF pleocytosis), usually involving the meninges, and less frequently resulting in meningoencephalitis which can lead to permanent neurological damage, including deafness (ref. 2).

Mumps immunization has been effective at controlling epidemic mumps infection. Following the licensure of the live virus mumps vaccine in 1967, the number of reported mumps cases in the United States decreased steadily, from 152,000 cases in 1968, to 2982 cases in 1985. This downward trend was reversed in 1986 to 1987, when a relative resurgence of mumps occurred. The resurgence appears to have been the result of incomplete vaccination coverage of adolescents and young adults in the years following the introduction of the live virus vaccine. In 1991, 4264 cases of mumps were reported, a 67% decrease from 1987.

At least 10 mumps vaccine strains, listed in Table 1 at the end of the descriptive text, are in use throughout the world. Strains have been adapted to the embryonated egg (ref. 3), chick embryo fibroblast cell culture (ref. 3 to 6) human diploid cell culture (ref. 7, 8) and quail embryo fibroblast cell culture (ref. 9). All strains appear to induce high levels of seroconversion.

Adverse reactions to mumps vaccination are rare and the most common are parotitis and low-grade fever. Vaccine-associated parotitis occurs most commonly 10 to 14 days after vaccination (ref. 10). Rash, pruritus, and purpura have been reported following mumps vaccination but are uncommon and usually mild and transient. Febrile seizures and deafness also have rarely been reported. One of the frequent complications of mumps infection is meningitis. Attenuated mumps vaccine strains have lost most of their potential for viremia and, therefore, for meningitis, but this potential has not been lost entirely. The vaccine strains in use today range widely in the rate of aseptic meningitis that occurs after vaccination from approximately 1 in 800,000 for the Jeryl Lynn strain (ref. 11) to as high as 1 in 1000 for the Leningrad-3 strain (ref. 12). In the United States, meningitis after vaccination with the Jeryl Lynn strain has been a rare event occurring after only one in 1,800,000 doses (ref. 13). In Germany, the same strain was associated with a meningitis rate of 1 in 1,000,000 doses (ref. 14). In Japan, the rate of meningitis following vaccination with the Urabe strain was 1 in 2000 doses, and the rate of meningitis with Urabe isolated from the cerebrospinal fluid was 1 in 9000 (refs. 15, 16). In Canada, the observed rate of meningitis after vaccination with the Urabe strain was calculated to be 1 in 62,000-doses (ref. 17). Data for the United Kingdom, based on Public Health Laboratory Service surveillance from all sources, suggested a rate of aseptic meningitis estimated at 1 in 11,000 doses of Urabe-containing vaccine (23 cases), compared with zero cases following inoculation with Jeryl Lynn-containing vaccine (ref. 18). Several countries, including European countries and Canada, have decided to discontinue use of the Urabe strain of mumps vaccine. Sequelae to post-vaccine meningitis have been rare or absent. The reason for the higher rate of vaccine associated disease for the Urabe Am9 vaccine is unknown. Sequence analysis of the SH genes (ref. 21, 22) as well as the matrix (M) and hemagglutinin-neuraminidase (HN) genes (ref. 23) of mumps isolates have not been able to identify a role for these genes in the attenuation of Urabe Am9 or the lack of attenuation associated with mumps isolates obtained following vaccine induced disease. Urabe Am9 vaccine was attenuated by six serial passages in chicken embryo amniotic cavity and two plaque isolations in quail embryo fibroblasts (ref. 36), as compared to the Jeryl Lynn strain of live attenuated mumps vaccine which was produced by 17 passages in embryonated chicken eggs followed by 10 passages in chicken embryo fibroblast culture (ref. 37).

In evaluating the importance of this complication, it has been argued that, if the Urabe strain is more immunogenic than the Jeryl Lynn strain, the risk-benefit equation may still be in favour of the Urabe strain (ref. 19, 20).

The HN gene is a major surface protein of mumps virus and is an important candidate gene with respect to vaccine failure. Afzal et al (ref. 23) have reported sequence analysis of the HN genes of the Urabe Am9 vaccine and vaccine-associated strains obtained from individuals with meningitidis and parotitis and these authors could not find sequence changes in the HN genes. In contrast, the present inventors compared the nucleotide sequence of the HN gene of the Urabe Am9 strain to clinical isolates associated with disease to determine whether sequence differences existed. It would be advantageous to provide a single substantially homogeneous Urabe mumps vaccine strain for use as a source of antigens in immunogenic preparations including vaccines, and immunogens and for the generation of diagnostic reagents.

SUMMARY OF THE INVENTION

The present invention is directed towards the provision of a homogeneous isolate of Urabe mumps virus and vaccines containing the same.

In accordance with one aspect of the present invention, there is provided a substantially homogeneous Urabe mumps virus strain characterized by having a codon encoding glutamic acid at amino acid position 335 of the haemagglutinin-neuraminidase (HN) protein thereof. Particularly, the codon is GAA but may be any other codon encoding glutamic acid. The presence of the glutamic acid encoding codon results in the abolition of a MseI restriction enzyme recognition site in the cDNA of native Urabe mumps virus strain, where the corresponding codon encodes lysine.

Such mumps virus strain may be one having the specific identifying characteristics of that deposited with the American Type Culture Collection (ATCC) located at 12301 Parklawn Drive, Rockville, Md., U.S.A., 20852, under ATTC Designation No. VR 2521 and, in particular, is such strain.

In this specification, the term "substantially homogeneous" means that the mumps virus is not contaminated with more than about 10%, preferably less than about 5% and most preferably less than about 1% of another Urabe mumps virus not having the characterizing codon.

The present invention also provides, in another aspect, an isolated and purified nucleic acid molecule (RNA or DNA) encoding the HN protein of a mumps virus strain and having a codon encoding glutamic acid at amino acid position 335 of the (HN) protein, particularly where the codon is GAA.

The novel mumps virus strain provided herein may be used as an active component of a mumps vaccine, which constitutes a further aspect of the invention. Preferably the vaccine contains a substantially pure homogeneous Urabe mumps virus strain, and may be devoid of any contamination with other Urabe mumps virus strain not having the characterizing codon.

The vaccine may be formulated as a microparticle capsule, ISCOM or liposome preparation. The vaccines may further comprise at least one other immunogenic or immunostimulating material and the immunostimulating material may be at least one adjuvant. Suitable adjuvants for use in the present invention include, (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein. Advantageous combinations of adjuvants are described in copending U.S. patent application Ser. No. 08/261,194 filed Jun. 16, 1994, assigned to Connaught Laboratories Limited and the disclosure of which is incorporated herein by reference.

The vaccines provided herein may be formulated to comprise at least one additional non-mumps immunogen, which may comprise or be derived from a paramyxovirus, Chlamydia, polio, hepatitis B, diphtheria toxoid, tetanus toxoid, influenza, haemophilus, pertussis, pneumococcus, mycobacteria and hepatitis A virus. Mumps vaccines are commonly provided as multivalent MMR vaccines, comprising, in addition to the mumps virus, at least one of attenuated or killed measles virus, attenuated or killed rubella virus, or subunits thereof. Such vaccines may further comprise an agent for protection against varicella or zoster infections.

In a further aspect of the invention, there is provided a method of immunizing a host against disease caused by mumps virus infection, comprising administering thereto an immuno-effective amount of a vaccine as provided herein. The immune response may be a humoral or a cell-mediated immune response. Hosts in which protection against disease may be conferred include mammals including primates including humans.

The present invention provides, in an additional aspect thereof, a method of producing a mumps vaccine, comprising administering the novel mumps virus provided herein to a test host to determine an amount and a frequency of administration of a vaccine containing the virus to elicit a protective immune response in the test animal, and formulating the vaccine in a form suitable for administration to a treated host in accordance with said determined amount and frequency of administration. The treated host may be a human.

A further aspect of the invention provides a method of determining the presence in a sample of antibodies specifically reactive with a mumps virus strain as provided herein, comprising the steps of:
 (a) contacting the sample with the mumps virus strain as provided herein to produce complexes comprising the mumps virus strain and any said antibodies present in the sample specifically reactive therewith; and
 (b) determining production of the complexes.

A further aspect of the invention provides a diagnostic kit for determining the presence of antibodies in a sample specifically reactive with the mumps virus strain provided herein, comprising:
 (a) the mumps virus strain as provided herein;
 (b) means for contacting the mumps virus strain with the sample to produce complexes comprising the mumps virus strain and any said antibodies present in the sample; and
 (c) means for determining production of the complexes.

In an additional aspect of the invention, there is provided a method of producing monoclonal antibodies specific for a mumps virus strain as provided herein, comprising:
 (a) administrating the mumps virus strain provided herein to at least one mouse to produce at least one immunized mouse;
 (b) removing B-lymphocytes from the at least one immunized mouse;
 (c) fusing the B-lymphocytes from the at least one immunized mouse with myeloma cells, thereby producing hybridomas;
 (d) cloning the hybridomas;
 (e) selecting clones which produce anti-mumps virus antibody;
 (f) culturing the anti-mumps virus antibody-producing clones; and then
 (g) isolating anti-mumps virus antibodies from the cultures.

The present invention further includes the use of the novel mumps virus strain provided herein as a pharmaceutical substance, particularly a vaccine for administration to a host susceptible to mumps infection.

In addition, the present invention includes the use of the mumps strain provided herein in the manufacture of a medicament for immunization against disease caused by mumps virus.

Advantages of the present invention include:
 a novel mumps virus strain useful for inclusion in vaccines for immunization against disease caused by mumps virus infection;
 an isolated and purified nucleic acid molecule encoding the HN protein of such novel mumps virus strain; and
 diagnostic kits and immunological reagents for specific identification of mumps virus in hosts infected thereby.

GENERAL DESCRIPTION OF INVENTION

Sequence analysis of the HN gene of the mumps virus has been effected, since, as noted above, it is a major surface protein of mumps virus. Previous sequence analysis of the HN genes of Urabe Am9 vaccine and vaccine-associated strains obtained from individuals with meningitis and parotitis did not locate sequence changes in the HN genes (ref. 23). We have compared the nucleotide sequence of the Urabe Am9 HN gene to clinical isolates obtained from vaccinees who developed meningitis or parotitis, to determine whether sequence differences could be detected that may be associated with vaccine associated disease.

As a result of such analysis, we have found that the Urabe Am9 vaccine is a mixture of mumps viruses that differ at a single codon of the HN gene. The wild-type HN gene nucleotide sequence has an A residue at nucleotide (nt) 1081, the resulting codon AAA encodes lysine at amino acid (aa) 335, whereas the variant HN sequence has a G residue at nt 1081 and, the resulting codon GAA encodes a glutamic acid residue.

Vaccination associated disease was, in most cases, only associated with the virus having wild-type form of the HN gene, indicating a strong selection in humans of virus with the wild type sequence relative to the variant type in humans. An implication of these data is that a vaccine composed entirely of the variant form would be safer than the existing mixed vaccine. Accordingly, we provide herein a substantially homogeneous Urabe mumps virus strain having a codon encoding glutamic acid at aa 335 of the HN protein. Such codon may be any encoding glutamic acid but is particularly GAA. The Urabe mumps vaccine strain is preferably a pure homogeneous strain and being devoid of any contamination with other Urabe mumps virus not having the characteristic codon.

The mutation at 1081 presumably affects one of the stages in virulence, such as spread, tropism, or ability to replicate in tissues and promote pathology (ref. 24). It is hypothesized that preparation in chicken embryo amniotic cavity or plaque isolation in quail embryos used to produce the attenuated Urabe Am9 strain, selected the G form of the HN gene and that this mutation confers an adaptive advantage in these hosts. However, selection or plaque purification may not have been complete, since the resulting vaccine represents a mixture of wild type and variant forms of the HN gene. Other mutations may also have occurred on adaption in quail embryo culture so that the A1081 form of Urabe Am9 is partially attenuated but that the G1081 form is more completely attenuated.

Evidence from studies with influenza virus supports the notion of incremental control of virulence and attenuation by several genes in virulent and attenuated variants. The A/FM/1/47-MA strain has acquired mutations in at least three genes that control virulence on 12 serial passages in mouse-lung (refs. 25, 26) as well as a mutation in one of its polymerase genes that controls interference (ref. 27). The ca A/AA/6/66 variant of influenza virus also possesses four mutant genes that control attenuation (ref. 28).

The Lys$^{335}$ to Glu$^{335}$ change resulting from the A to G substitution at nt 1081 leads to a reversal of charge at this position consistent with a change in protein conformation, and possibly function. This change occurs in a conserved region of HN that is adjacent to a known neutralization epitope between codons 352 to 360 in the Kilham strain of mumps virus, which was identified by the generation of neutralization escape mutants using a single monoclonal antibody (ref. 29). This same monoclonal antibody also inhibited hemagglutination and neuraminidase activities of the Kilham virus, indicating that these functional sites are close to each other on the HN protein (ref. 30). Also of relevance is the location of an amino acid substitution Leu$^{332}$→Arg$^{332}$ in the attenuated JL2 form of Jeryl Lynn vaccine (nomenclature of Afzal et al, ref. 31) relative to its contemporary North American wild-type strains. This substitution results in a similar though less dramatic change from an uncharged to a positively charged residue three amino acids from the change seen in the variant form of Urabe. Attenuated vaccines are produced by adaptation to growth in an alternate host or cell type. The mutations that result in adaptation to the new host are responsible for attenuation for the human host. It is hypothesized that the Lys$^{335}$→Glu mutation confers improved replication of mumps virus for quail embryo fibroblast cells or chicken amniotic cells with a concomitant decrease in ability to replicate in humans. Other mutations could also have occurred on adaption in quail embryo so that the A1081 form of Urabe AM9 is partially attenuated but the G1081 form is more completely attenuated. It was surprising that the Urabe AM9 vaccine constituted a mixture of genetic forms since it was produced by two successive plaque purifications on quail embryo fibroblasts following six passages in chicken embryo amniotic cavity (refs. 36, 38). It is possible that the plaque purification was not effective and thus the virus obtained following two cycles of plaquing was itself a mixture or, alternatively, that subsequent passage in chicken embryo to prepare vaccine stocks resulted in selection of one or other of the forms. Replication of Urabe Am9 vaccine in Vero cells favours replication of the variant form over the wild type form suggesting that at least a subset of the G1081 form has a selective growth advantage in this cell type. The fact that plaque purified isolates of the G1081 form did not have a growth advantage relative to purified A1081 form in Vero cells relative to the clinical isolates suggests that more than one genetic type of virus with G1081 exists and that they differ in growth properties in Vero cells, since a population of G1081 genotype viruses has a selective advantage or passage in Vero cells.

It is clearly apparent to one skilled in the art, that the various embodiments of the present invention have many applications in the fields of vaccination, diagnosis, treatment of mumps virus infections and the generation of immunological reagents. A further non-limiting discussion of such uses is further presented below.

1. Vaccine Preparation and Use

Immunogenic compositions, suitable to be used as vaccines, may be prepared from the novel mumps virus strain as disclosed herein. The immunogenic composition elicits an immune response which produces antibodies, including anti-mumps virus antibodies.

Immunogenic compositions, including vaccines, may be prepared as injectables, as liquid solutions or emulsions. The mumps virus strain may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active ingredient(s) in the range of about 0.5 to about 10 wt %, preferably about 1 to 2 wt %. Oral formulations may include normally employed incipients such as, for example, pharmaceutical grades of saccharine, cellulose and magnesium carbonate.

The immunogenic compositions, including vaccines, provided can take the form of solutions, suspensions, tablets, pills, capsules, sustained release formulations or powders and contain about 1 to 95 wt % of the mumps vaccine, preferably about 20 to about 75 wt %.

The immunogenic preparations and vaccines are administered in a manner compatible with the dosage formulation, and in such amount as will be immunogenic, therapeutically effective and protective. The quantity to be administered depends on the subject to be treated, including, for example, the capacity of the individual's immune system to synthesize antibodies, the degree of protection desired and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage may also depend on the route of administration and will vary according to the size of the host.

The concentration of the mumps virus strain in an immunogenic composition according to the invention is in general about 1 to 95 wt %, preferably about 20 to 75 wt %. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens. As noted previously, attenuated mumps virus often is combined with measles virus and rubella virus in a multivalent MMR vaccine.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria present in many vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

2. Immunoassays

The mumps virus strain of the present invention is useful as an antigen in immunoassays including enzyme-linked immunosorbent assays (ELISA), RIAs and other non-enzyme linked antibody binding assays or procedures known in the art for the detection of anti-mumps virus strain antibodies. In ELISA assays, the mumps virus strain is immobilized onto a selected surface, for example, a surface capable of binding viruses such as the wells of a polystyrene microtiter plate. After washing to remove incompletely adsorbed material, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound mumps virus strain, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a spectrophotometer.

BIOLOGICAL DEPOSITS

A mumps virus provided in accordance with aspects of the present invention has been deposited with the American Type Culture Collection (ATCC) located at 12301 Parklawn Drive, Rockville, Md., USA, 20852, pursuant to the Budapest Treaty and prior to the filing of this application. Samples of the mumps virus strain will become available to the public upon grant of a patent based on this United States Patent Application. The invention described and claimed herein is not to be limited in scope by the strain deposited, since the deposited embodiment is intended only as an illustration of the invention. Any equivalent or similar mumps virus strains are within the scope of the invention.

| | Deposit Summary: | |
|---|---|---|
| Strain | ATCC Designation | Date Deposited |
| Mumps virus, G1081 | VR 2521 | January 16, 1996 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Example 1

This Example describes cell lines, viruses and vaccines used.

African green monkey Vero cells were obtained from the Bureau of Biologics, Health and Welfare Canada, and were maintained in autoclavable Minimal Essential Medium (MEM, Gibco) supplemented with 2 mM L-glutamine and 7% fetal bovine serum (FBS, Gibco). The human amnion cell line, FL, was purchased from ATCC, and maintained in MEM supplemented with 10% FBS.

Post-vaccination isolates of mumps BB871004 (1004), BB871005 (1005), BB870716 (716), BB870717 (717), BB870718 (718), BB870719 (719), BB870888 (888), BB870889 (889), BB870890 (890), and the wild-type isolates KS/67 (KS), CA/73/67 (CA) and BB870891 (891) were all obtained from the Bureau of Biologics, Health and Welfare Canada as well as the Jeryl Lynn vaccine (JL), (Merck Sharpe and Dohme lot #6). The Jeryl Lynn (JL) vaccine was provided from the Bureau of Biologics, Health and Welfare Canada. Two lots of Urabe Am9 vaccines were obtained, one from Pasteur Merieux, Lyon, France (URA/PM) (Lot #JO547) and another commercial preparation from SmithKline Beecham (URA/SKB) (lot #MP09A44) that had been distributed in Canada prior to 1989. The source and history of the mumps viruses are shown in Table 2 below.

Stock of all viruses were prepared by infecting Vero monolayers at a moi of 0.05 to 0.1 on day 0 and then harvesting supernatants at day 5. Stocks were titrated on Vero monolayers as follows. Serial dilutions of virus were plated on 6-well plates, overlaid with 0.6% Noble agar/0.01 DEAE Dextran in 199 Medium (Gibco) supplemented with 7% FBS. At day 4, wells received a second overlay with the addition of 0.1% Neutral red, and plaques were counted after another 24 hours.

Example 2

This Example describes the production, cloning and sequencing of mumps virus cDNA.

Mumps virus was concentrated from cell culture supernatant by PEG precipitation. RNA was extracted, reverse transcribed and amplified by PCR and cloned as described previously (ref. 32). The whole HN gene was amplified as 2 or 3 overlapping pieces using 2 or 3 sets of primers in various combinations; (mumps sequences were taken from ref. 39 and are underlined) 5'-2 (5'-CACGGATCCCACAGGTAGAATTGGAATTC-3' (SEQ ID No: 10), genome sense HN gene positions 1783–1803); HN 5'+212 (5'-TATATTGGTTATTGTCAC-3' (SEQ ID No: 11) complimentary to HN gene positions 212–229); SH+3246 (5'-ATCGGATCCAGCGATCCTGCTCTCGCT-3' (SEQ ID No: 12) complementary to SH gene 184–201); HN-751 (5'-TTGAACATAGGATACCCT-3' (SEQ ID No: 13) genome sense HN gene positions 734–751); SBL+1475 (5'-ATATATTCATTCACTCGT-3' (SEQ ID No: 14) complementary to HN gene positions 1475–1492); and HN5'-(5'-ACGCTCGAGCGCCATTCTGGCCTG-3' (SEQ ID No: 15) contains a Xho I adaptor adjacent to the L gene positions 1 to 14 in genome sense plus the L-HN intergenic G).

Double-stranded cDNA clones were sequenced by the dideoxynucleotide chain-termination method of Sanger (ref. 33) using the Sequenase Kit (USE) and $^{35}$S-daTP. Direct cDNA sequencing of PCR products was performed using the modification of Winship (ref. 34) where DNA was denatured by boiling and immediately cooled before proceeding with the labelling reaction omitting the primer annealing step. Sequence ladders were produced by electrophoresis in 0.2 mm thick, 6% acrylamide, TBE gels.

Each HN gene was 1893 nucleotides long with an open reading frame from position 79 to 1824 encoding a 582 amino acid protein. Table 3 below shows a matrix of nucleotide and amino acid sequence homology for the HN genes of those viruses examined in this study as well as published sequences for the Japanese wild-type strain, Miyahara, the RW wild-type strain from the USA, and the SBL laboratory strain isolated in the USA.

Figure 1:
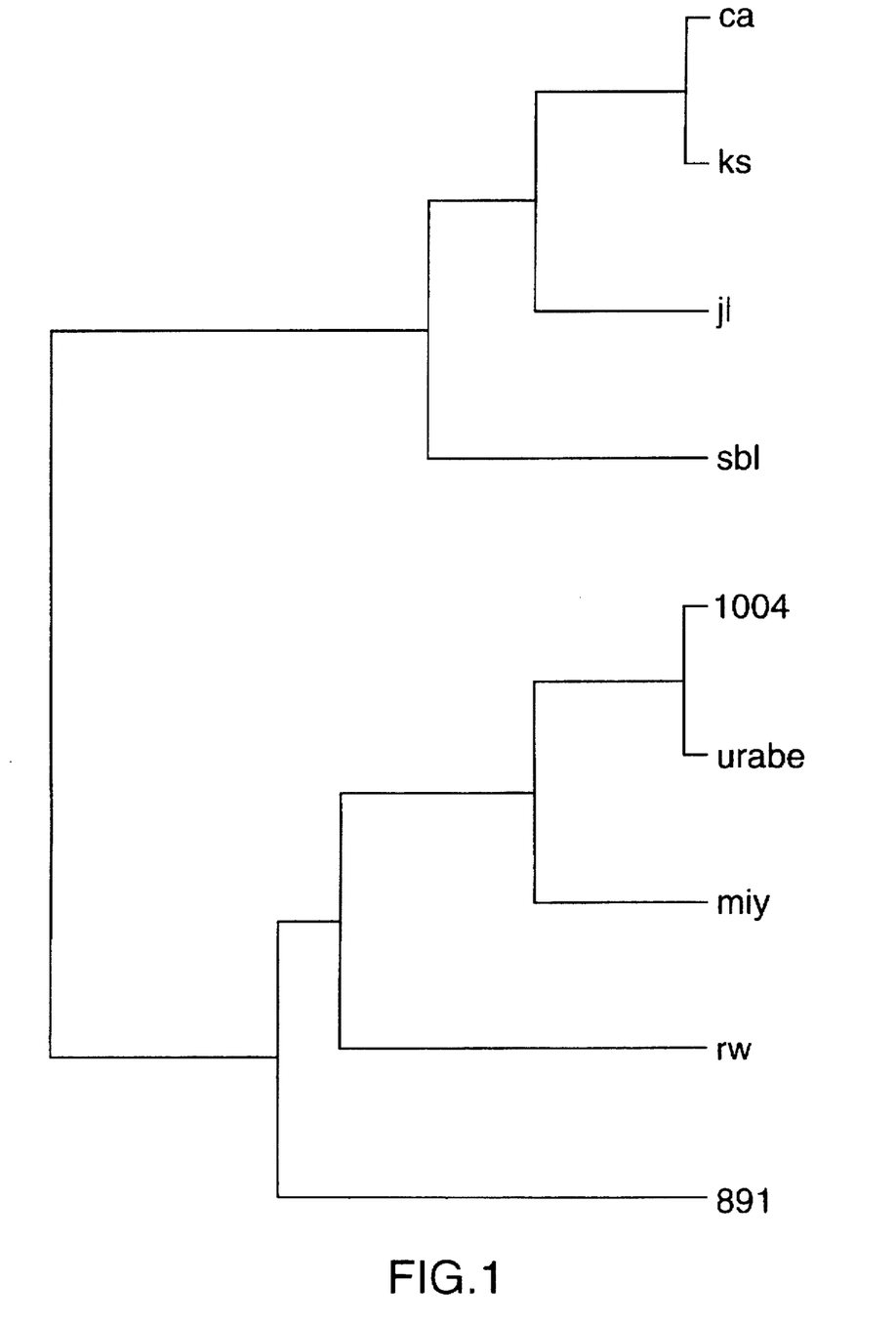
FIG. 1 is a dendogram showing the most similar pairwise combinations of HN genes of mumps virus strains URA/SKB (Urabe)
Figure 2A:
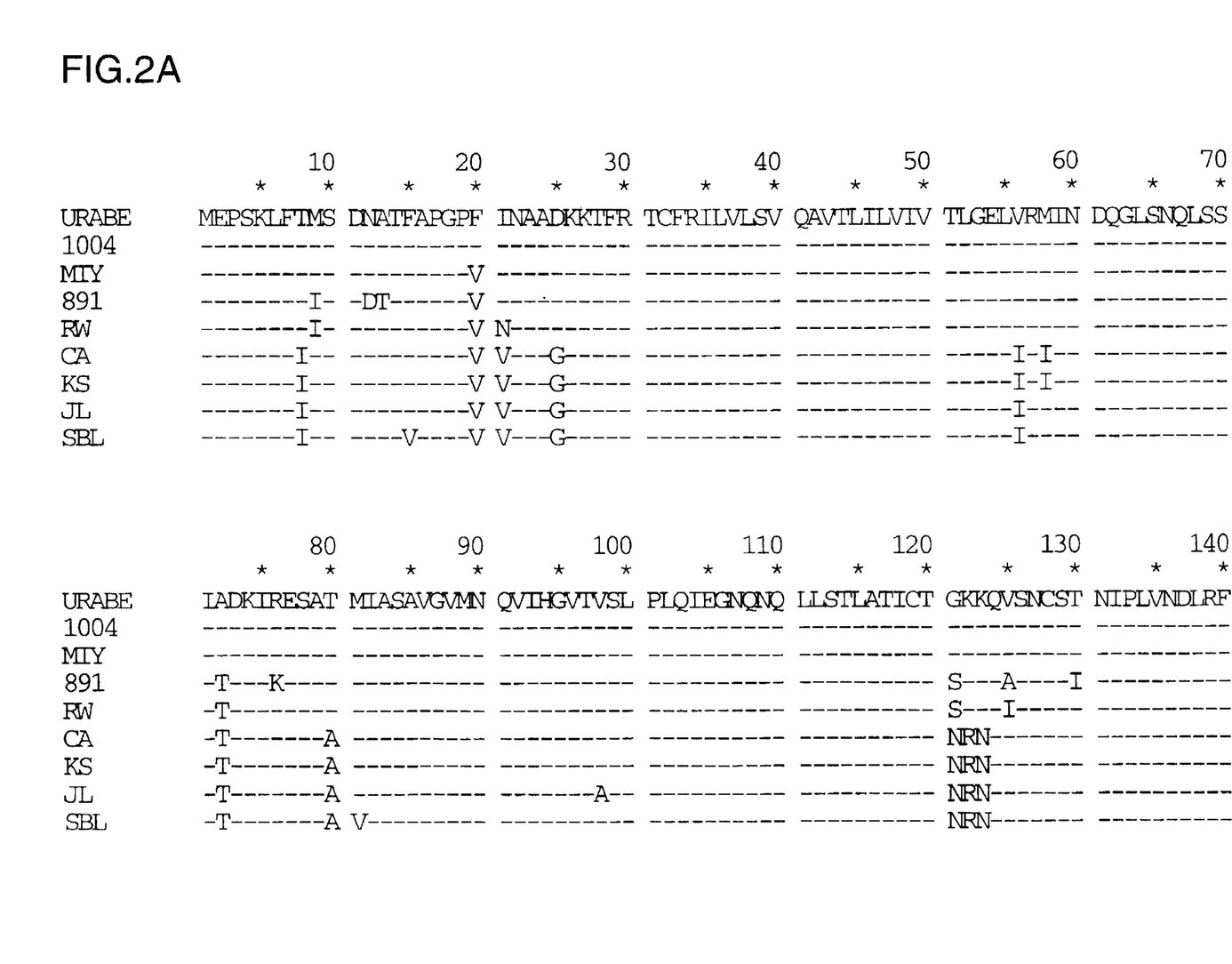
FIG. 2 is an amino acid sequence alignment of HN proteins from a variety of mumps virus strains (SEQ ID Nos: 1 to 9)
Figure 2B:
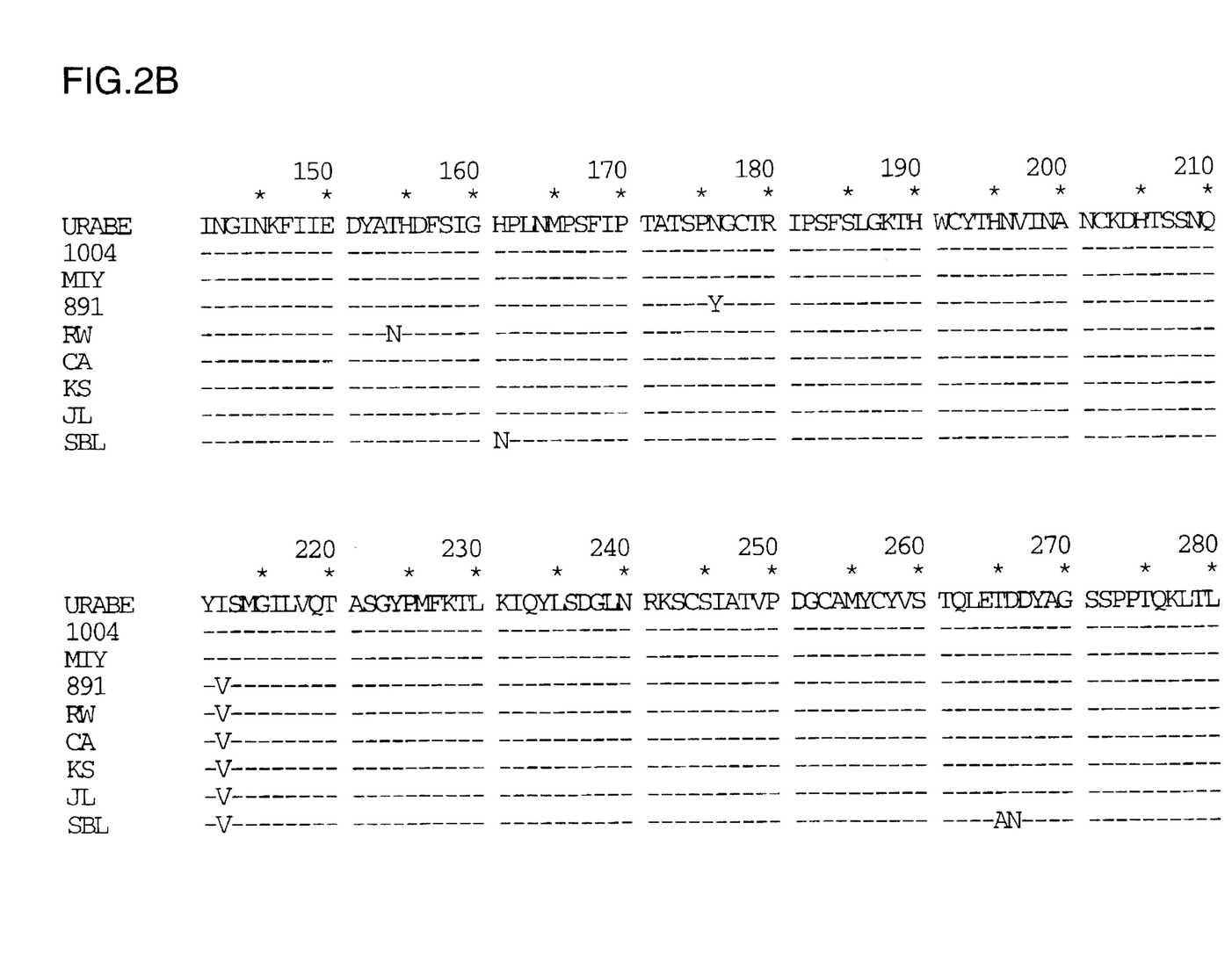
Figure 2C:
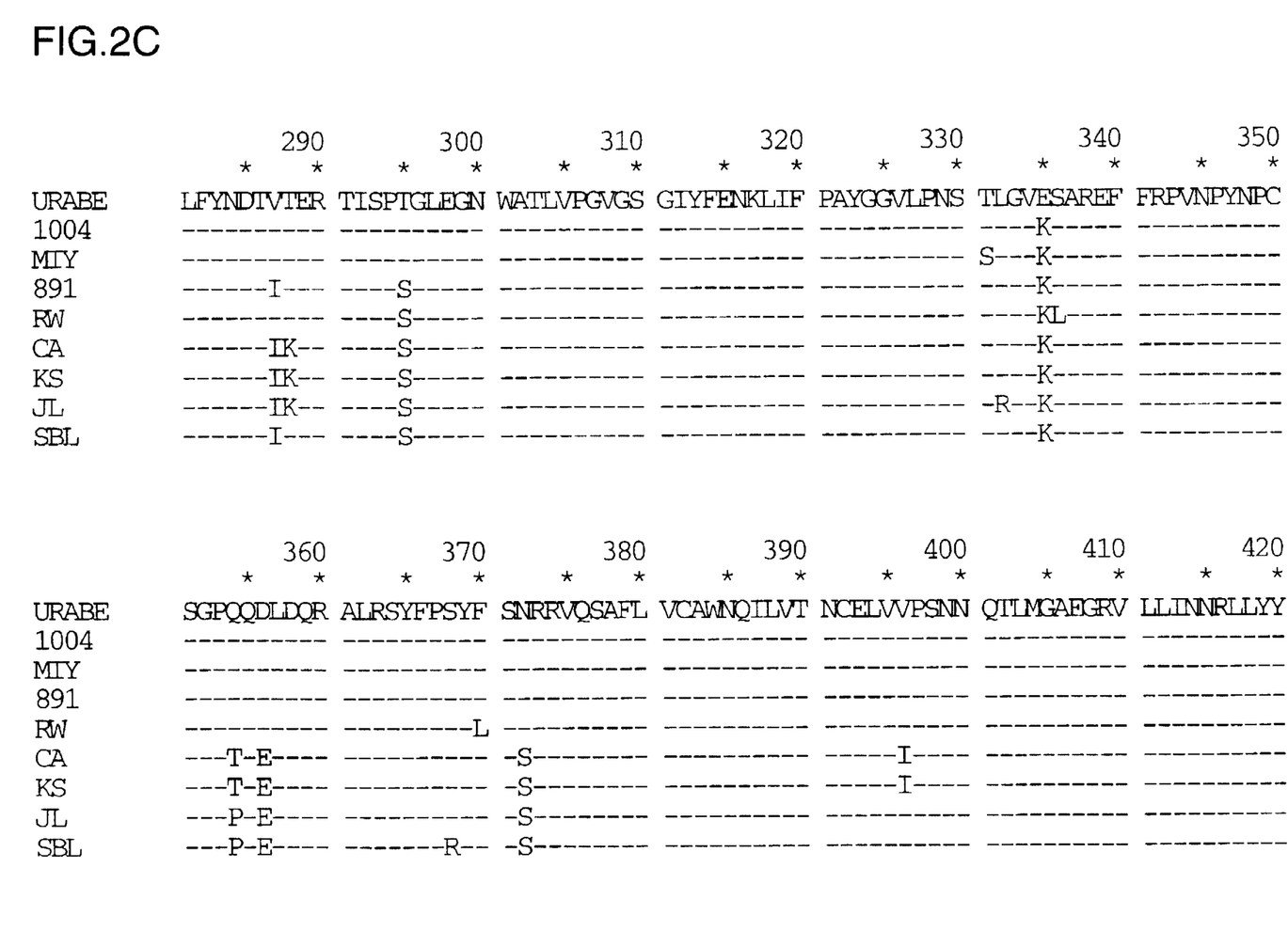
Figure 2D:
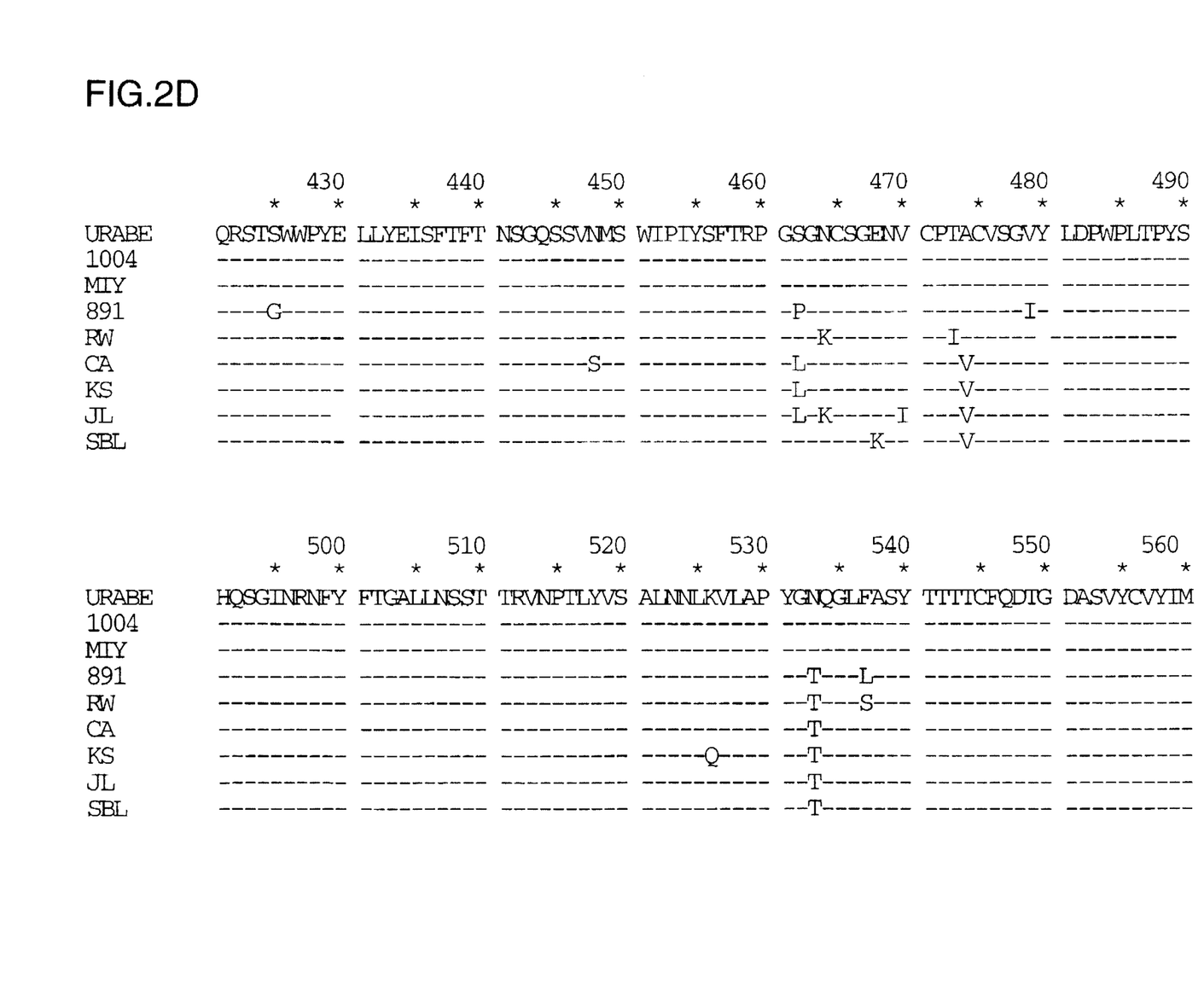
Figure 2E:
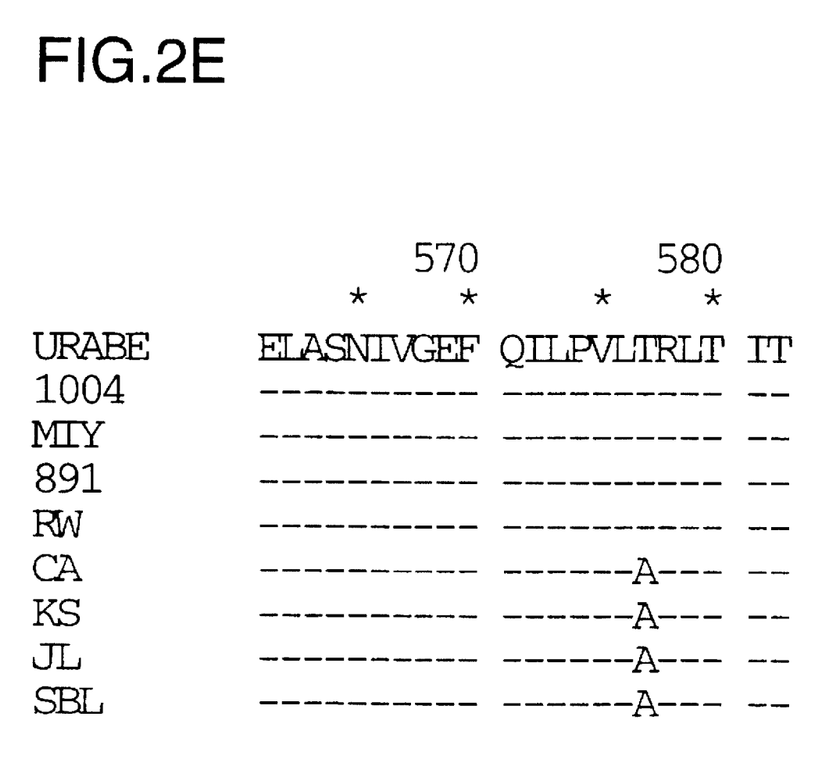

In a dendogram that shows the most similar pairwise sequence comparisons of these genes (FIG. 1) two major groupings were formed: one group composed of the older North American strains and their derivatives, CA, KS, SBL and JL vaccine, with the other group composed of two subgroups, the Japanese isolates and the more recent North American isolates, RW and 891.

Two clones of JL were sequenced and had identical nucleotide sequences. Both were the JL2 form since there were 137 nucleotide differences from Urabe Am9 similar to the 136 nucleotide changes reported by Afzal et al (ref. 23). The post-vaccination meningitis isolates, 1004 and 1005, were identical, both possessing two nucleotide differences compared to Urabe Am9, only one of which produced a coding change due to a $A_{1081} \rightarrow G$ substitution relative to the Urabe Am9 sequence. When compared to other isolates, 1004 and 1005 had a wild-type genotype with regard to nt 1081. Comparison of the predicted amino acid sequences showed that the single nucleotide change $A_{1081}$ to G (wild-type to variant) resulted in a Ly$^{335}$ (AAA) residue being changed to Glu$^{335}$ (GAA), suggesting that the Urabe Am9 vaccine may have acquired this mutation on attenuation during quail embryo passage (FIG. 2 contains a deduced amino acid sequence alignment of the HN protein from a variety of mumps strains, as determined herein). The Jeryl Lynn vaccine strain also possessed an amino acid substitution three residues away, Leu$^{332}$→Arg, that could be operating to attenuate this vaccine. This region of HN showed some variation in two mumps strains with a conservative change in Miyahara Thr$^{331}$→Ser and a Ser$^{336}$→Leu substitution in RW.

The HN sequences of both post-vaccination isolates differed from Urabe Am9, having an A rather than a G at nt 1081. Sequence analysis of four additional HN cDNA clones of Urabe Am9 vaccine indicated that two clones had the variant codon GAA and two had the wild-type codon AAA. The HN sequence of all of these cDNAs possessed characteristic sequence features that were identical to Urabe Am9 virus HN sequence at the other nucleotide positions other than position 1081 between nucleotides 1030 and 1280, obviating the possibility of contamination by cDNA clones derived from other mumps viruses in the laboratory.

Figure 3:
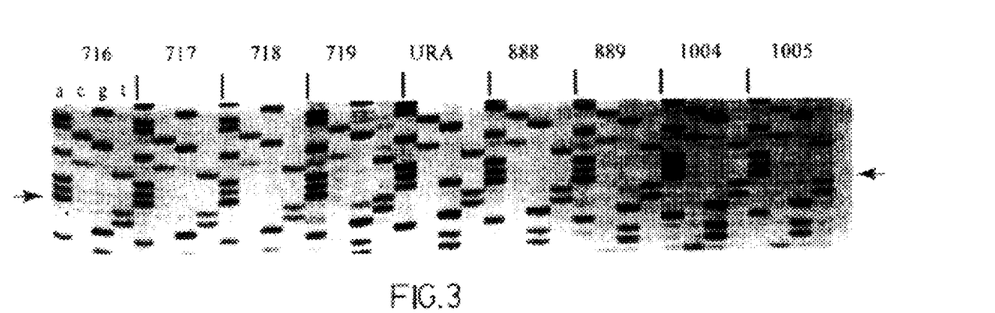
FIG. 3 shows sequencing ladders obtained for three post vaccine meningitis isolates (1004, 1005 and 719) and five post-vaccination parotitis cases (716, 717, 718, 888 and 889) as well as URA/SKB vaccine virus (Vero cell passage 3). The position of nucleotide 1081 is marked with an arrow.

It is apparent from this analysis that the Urabe Am9 vaccine is a mixture of viruses that differs in sequence at nt 1081 of the HN gene. To further assess the heterogeneity or homogeneity of sequence at this position for the vaccine (passage three in Vero cells) and post vaccine isolates, sequencing was performed directly on the pool of cDNA produced by RT/PCR of viral RNA. FIG. 3 shows sequencing ladders obtained for three post vaccine meningitis isolates (1004, 1005 and 719) and five post-vaccination parotitis cases (716, 717, 718, 888 and 889) as well as URA/SKB vaccine virus (Vero cell passage 3).

The HN sequence for the Urabe Am9 vaccine has both an A and a G at position 1081 whereas all post vaccine isolates from patients only possessed an A at this position. This observation indicates that immunization of individuals with Urabe Am9 vaccine that is a mixture of viruses differing at nucleotide 1081 leads to the selection of the strains(s) possessing an A at this position at least in instances of vaccine-associated disease.

Example 3

This Example describes the quantitation of Urabe Am9 virus types in vaccine lots.

Figure 4:
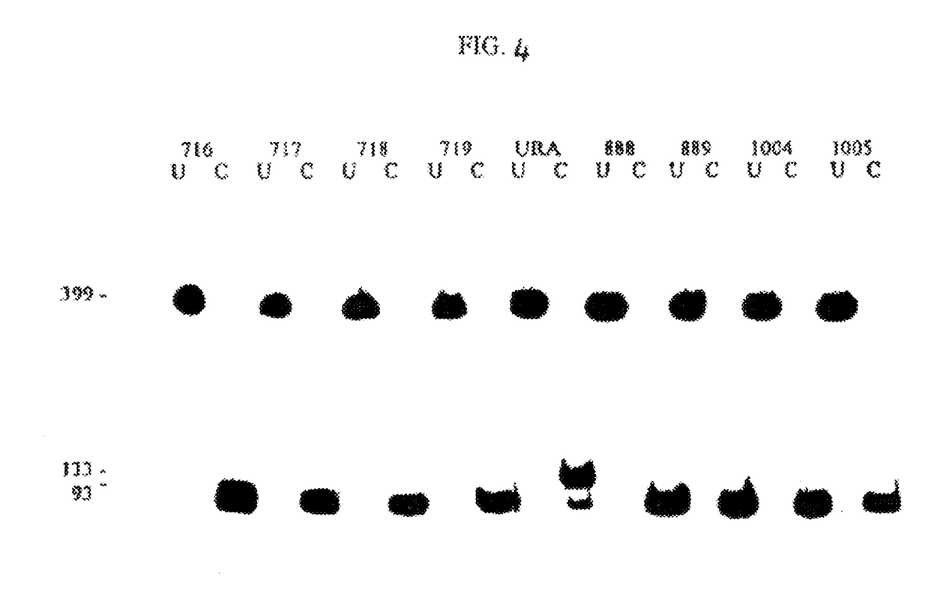
FIG. 4 shows quantification of the proportion of A versus G at nucleotide position 1081 of the HN gene of the vaccine and post-vaccination isolates associated with meningitis and parotitis. Mse I cleavage of 429 nucleotide long, end-labelled RT-PCR products that spanned nucleotide 1081 of HN genes were analyzed by TBE PAGE (8% acrylamide). Digestion of HN cDNA containing an A at nucleotide 1081 resulted in a 132 nucleotide fragment whereas those containing a G at this position yielded a 162 nucleotide product. U indicates uncleaved and C indicates MseI digested DNA. This Figure is a composite of two gels since some samples were repeated due to incomplete restriction digestion.

The nucleotide change, $A_{1081}$ to G, seen in Urabe Am9 as detailed above results in the loss of an MseI restriction endonuclease cleavage site by the change TTAA to TTGA. This was used to quantify the relative abundance of the A and G forms in mumps virus stocks by MseI cleavage of end-labelled mumps virus cDNA produced by RT/PCR. To measure the level of G or A at nt 1081 short end-labelled cDNA molecules were produced by PCR and digested with Mse I before analysis by PAGE. The wild type sequence is cleavable whereas the "G-form" is resistant to cleavage. PCR of mumps CDNA was done using 5' labelled SBL+985 primer (plus sense HN positions 948–966, 5'-GACAATATCTCCATCTGG-3' (SEQ ID No: 16)) and unlabelled SBL 1384-(minus sense HN positions 1356–1376 5'-ATAGAGGAGTTCATAGGG-3' (SEQ ID No: 17)). Primer (100 ng) was end-labelled using 50 μCi of gamma $^{32}$p ATP (7000 Ci/mmol) and T4 polynucleotide kinase, (ref. 35). A portion of the PCR product (2 μl) was digested in a 20 ul reaction with 2.5 U of Mse I overnight. The wild type mumps sequence has two Mse I cleavage sites, at position 132 and 162 from the labelled 5' end of the 429 nucleotide PCR product, whereas the mutant form has only one site at position 162. The only labelled cleavage product from the wild type sequence is 132 bp long and from the mutant form is 162 bp. The proportion of the two forms was determined by quantitation of the two forms resolved on 8% acrylamide gels containing tris-borate EDTA. Polyacrylamide gel electrophoresis was used to detect the 132 nt band resulting from cleavage and a 162 nt band resulting from resistance to cleavage at the Mse I site, containing nt 1081 of the HN gene (FIG. 4). The total conversion of full-length PCR product to smaller forms indicated that restriction digestion was complete. Scintillation counting of excised restriction fragment bands allowed quantification of variant and wild-type mumps virus that differ at nucleotide 1081. In Table 4, the percentages of variant and wild-type forms seen in Urabe Am9 vaccine from SmithKline Beecham (SKB), Lot #MP09A44K, Pasteur Merieux (PM), Batch J0547, Vero cell passage three of the SKB vaccine, three post-vaccination mumps meningitis isolates, and five post-vaccination parotitis isolates are shown. All of the vaccine stocks were mixtures of the two HN sequences at nt 1081, although the relative proportions of the A and G forms varied, presumably due to differences in passage history. All of the post-meningitis isolates and most (3/5) post-parotitis isolates only possessed the A at nt 1081, whereas the other two parotitis isolates had 2% G and 98% A at this position.

The SKB Am9 vaccine had an increased level of the variant (G) form when compared to the vaccine preparations following three passages in Vero cells, suggesting a selection of the variant form in Vero cells. This is opposite to the selection for the wild-type form occurring in post-vaccination disease, since all of the mumps virus isolates obtained from cases of meningitis and parotitis possessed an A at nt 1081.

To assess the extent of selection of the variant type relative to the wild type in Vero cells, an aliquot of freshly reconstituted vaccine was used to infect Vero cells, and aliquots were collected at each of five serial undiluted passages. The relative amounts of the A and G forms of the HN sequence were determined by Mse I digestion of CDNA. Table 5 shows that the relative proportion of variant G form increased with passage in Vero cells from 25% in the vaccine preparation to 63% after five passages. Thus the variant form has a replicative advantage in Vero cells over the wild-type form.

Example 4

This Example describes the growth characteristics of Urabe Am9 virus types.

Because passage in different cell lines resulted in selection of different forms of the virus, growth characteristics of the viruses were examined in these same cell lines. The variant (G) and wild type (A) forms of mumps virus were plaque purified from Urabe Am9 (lot #JO547 of Pasteur Merieux). Of 10 plaques that were selected, four of the 1081 form (A3, A5, A9, A10) and four of the G1081 form (E1, E2, E4, E7) were obtained and two plaques contained mixtures of both forms as determined by Mse 1 digestion. The eight homogeneous plaques were subjected to a second cycle of plaque purification. The yield of infectious virus in Vero cells was determined for each of the plaque purified viruses, as well as for the Urabe Am9 vaccine (SKB lot MP09A44K Vero passage 3) which primarily has the variant HN sequence (>80%), and post vaccination meningitis isolates #1004 and #1005 which had 100% wild-type HN sequence at HN nt 1081. A wild isolate of mumps, 891, was also included in some experiments. Despite the fact that the variant HN sequence is preferentially selected after growth in Vero, the Urabe Am9 strain, with >80% variant HN sequence, consistently grows to 1 log lower titres than the post-vaccine meningitis isolates, and the wild isolates (Table 6). The growth of the plaque purified A and G forms yielded intermediate levels of infectious virus with titres between those obtained for the Urabe Am9 vaccine virus and lower than the titres of the post-vaccination isolates and wild isolate, with the exception of isolate 3A, which grows less well than the vaccine virus (Table 6). These results suggest that the growth differences between the post-vaccine and Urabe Am9 viruses are not due solely to the A to G change at nt 1081 of the HN gene and that the A1081 form of Urabe Am9 selected in vaccinees who developed clinical disease were genetically heterogenous at other sites in the genome.

SUMMARY OF THE DISCLOSURE

In summary of this disclosure, the present invention provides a novel attenuated substantially homogeneous Urabe mumps virus strain characterized by having a codon encoding glutamic acid at amino acid position 335 for the haemagglutination neuraminidase (HN) protein, as well as a gene encoding this HN Glu-335 protein. Modifications are possible within the scope of this invention.

TABLE 1

Mumps Vaccine Strains

| Strain | Manufacturer | Cell Substrate | Main Area of Distribution |
|---|---|---|---|
| Jeryl Lynn | Merck | CEF | USA, UK |
| Urabe | SmithKline Beecham | CEF | Europe |
|  | Pasteur Merieux SV | CEF | Europe |
|  | Biken | CEF | Japan |
| Hoshino | Kitasato Institute | CEF | Japan |
| Rubini | Swiss Serum Institute | HEF | Switzerland |
| Leningrad-3 | Bacterial Medicine Institute, Moscow | QEF | Former USSR |
| L-Zagreb | Institute of Immunology of Zagreb | CEF | Former Yugoslavia |
| Miyahara | Chem-Sero Therapeutic Research Institute | CEF | Japan |
| Torii | Takeda Chemicals | CEF | Japan |
| NK M-46 | Chiba | CEF | Japan |
| S-12 | Razi State Serum & Vaccine Institute | HEF | Iran |

CEF, Chick embryo fibroblast; HEF, human embryonic fibroblast; QEF quail embryo fibroblast.

TABLE 2A

Source and history of mumps viruses used in this specification

| Virus isolate | Source | Site of isolation | Clinical feature | Vaccination |
|---|---|---|---|---|
| BB#871004 | CANADA | CSF | MENINGITIS | MMR* |
| BB#871005 | CANADA | CSF | MENINGITIS | MMR* |
| BB#870719 | CANADA | CSF | MENINGITIS | MMR* |
| BB#870716 | CANADA | THROAT | PAROTITIS | MMR* |
| BB#870717 | CANADA | THROAT | PAROTITIS | MMR* |
| BB#870718 | CANADA | THROAT | PAROTITIS | MMR* |
| BB#870888 | CANADA | THROAT | PAROTITIS | MMR* |
| BB#870889 | CANADA | THROAT | PAROTITIS | MMR* |
| KS/67 | ONTARIO/1967 | THROAT | PAROTITIS | NONE |
| CA/73/67 | ALBERTA/1967 | THROAT | PAROTITIS | NONE |
| BB870891 | ALBERTA/1982 | THROAT | PAROTITIS | NONE |

*Trivalent MMR vaccine containing URA/SKF

TABLE 2B

Vaccine Preparations

| | |
|---|---|
| JERYL LYNN | COMMERCIAL VACCINE MERCK SHARP AND DOHME (LOT #6), (JL) |
| URABE AM9 | COMMERCIAL VACCINE SMITHKLINE BEECHAM (LOT MP09A44K), (URA/SKB) |
| URABE AM9 | COMMERCIAL VACCINE PASTEUR MERIEUX (BATCH J0547), (URA/PM) |

TABLE 3

Pairwise comparisons of nucleotide and amino acid sequence differences of HN genes from mumps viruses.

| | NUCLEOTIDE | | | | | | | | |
|---|---|---|---|---|---|---|---|---|---|
| | CA | KS | JL | SBL | 1004 | URABE | MIY | RW | 891 |
| CA | — | 3 | 20 | 45 | 141 | 141 | 138 | 138 | 143 |
| KS | 2 | — | 21 | 46 | 142 | 142 | 139 | 139 | 144 |
| JL | 5 | 5 | — | 37 | 137 | 137 | 133 | 130 | 141 |
| SBL | 9 | 9 | 10 | — | 130 | 130 | 126 | 126 | 134 |
| 1004 | 15 | 15 | 17 | 17 | — | 2 | 28 | 65 | 79 |
| URABE | 16 | 16 | 18 | 18 | 1 | — | 28 | 67 | 79 |
| MIY | 15 | 15 | 17 | 17 | 2 | 3 | — | 63 | 76 |
| RW | 17 | 17 | 17 | 19 | 10 | 11 | 10 | — | 77 |
| 891 | 15 | 15 | 17 | 18 | 9 | 10 | 9 | 11 | — |
| | AMINO ACIDS | | | | | | | | |

Cloned cDNA copies of HN genes of URA/SKB vaccine, (Urabe), JL vaccine, post-vaccination meningitis isolate 1004, and the wild isolates KS, CA, and 891, were sequenced. The amino acid sequences were deduced from the nucleotide sequence and are shown below the diagonal formed by the identical comparisons; shown as (—). Published sequences of the SBL, Miyahara (MIY), and RW strains are included for comparison.

TABLE 4

Relative Proportion of Wild Type and Variant Mumps Virus in HN Mumps Vaccines and Clinical Isolates from Cases of Post-Vaccination Disease.

| VIRUS STOCK | SEQUENCE AT NT 1081 | PROPORTION OF VARIANT "G" | PROPORTION OF WILD-TYPE "A" |
|---|---|---|---|
| URABE AM9 PM #J0547 | G AND A | 54% | 46% |
| URABE AM9 SKB#MP09A44K | G AND A | 25% | 75% |
| SKB#MP09A44K VERO P3 | G AND A | 80% | 20% |
| SKB MENINGITIS #87719 | A | UD* | 100% |
| SKB MENINGITIS #871004 | A | UD | 100% |
| SKB MENINGITIS #871005 | A | UD | 100% |
| SKB PAROTITIS #87716 | A | UD | 100% |
| SKB PAROTITIS #87717 | A | 2% | 98% |
| SKB PAROTITIS #87718 | A | 2% | 98% |
| SKB PAROTITIS #87888 | A | UD | 100% |
| SKB PAROTITIS #87889 | A | UD | 100% |

*UD = Undetectable

TABLE 5

Selection of Variant Type Urabe Am9 on Serial Passage in Vero Cells

| PASSAGE NO. OF URABE VACCINE (SKB LOT MP09A44K) | PERCENTAGE OF G AT NO 1081 | PERCENTAGE OF A AT NT 1081 |
|---|---|---|
| P0 | 25 | 75 |
| P1 | 37 | 63 |
| P2 | 49 | 51 |
| P3 | 55 | 45 |
| P4 | 68 | 32 |
| P5 | 63 | 37 |

TABLE 6

Titres of Mumps Isolates after Growth in Vero Cells

| VACCINE & VACCINE-LIKE (GLU 335) | WILD & WILD-LIKE (LYS 335) |
|---|---|
| URA/SKB (Vero P3): $2.1 \pm 0.8 \times 10^6$ (8) | 1004: $3.6 \pm 2.4 \times 10^7$ (7) |
| | 891: $4.2 \pm 1.8 \times 10^7$ (3) |
| | 890: $3.1 \pm 2.2 \times 10^7$ (3) |
| Purified plaques: | Purified plaques: |
| G2: $4.4 \pm 2.6 \times 10^6$ (6) | A3: $4.9 \pm 0.8 \times 10^5$ (2) |
| G4: $2.4 \pm 1.3 \times 10^6$ (6) | A5: $3.0 \pm 1.9 \times 10^6$ (5) |
| G7: $2.6 \pm 0.6 \times 10^6$ (3) | A9: $5.5 \pm 3.3 \times 10^6$ (6) |

Vero monolayers were infected at an moi of 0.05. Supernatants were collected and titrated on Vero monolayers at day 5 post infection. The stock of vaccine virus was prepared by 3 passages in Vero cells; 1004 is a post-vaccination meningitis isolate, 890 is post-vaccination parotitis isolate, and 891 is a wild isolate. Values represent means ± standard deviations, numbers of replicates are given in parentheses.

REFERENCES

1. Wolinsky J. S., Server A. C., Mumps virus. In Fields B. N., Knipe O. M., Chanock R. M., Hirsh M. S., Melnick J. L., et al. (eds). Virology. New York, Raven Press, 1985, pp. 1255–1284.
2. Wolinsky, J. S. and M. N. Waxham. 1990, Mumps virus in Fields Virology Vol. 1, 2nd Edition. pages 989–1012 (B. N. Fields and D. Knipe Eds.) Raven Press, New York.
3. Beck M., Weisz-Malecek R., R. Mesko-Prejc M., Radman V., Juzbasic M., Rajninger-Miholic M., Prislin-Musklic M., Dobrovsak-Sourek V., Smerdet S., Strainer D. W. Mumps vaccine L-Zagreb, prepared in chick fibro-blasts. I. Production and field trials. J Biol Stand 17:85–90, 1989.
4. Buynak E. B. , Hilleman M. R. Live attenuated mumps virus vaccine. 1. Vaccine development. Proc Soc Exp Biol Med 123:768–775, 1966.
5. Sasaki %., Hagashihara M., Inoue K., Igarashi Y. Makillo S. Studies on the development of a live attenuated mumps vaccine. 1. Attenuation of the Hoshino "wild" strain of mumps virus. Kitasato Arch Exp Med 49:43–52, 1976.
6. Makino S., Sasaki K., Nakayama T., Oka S., Urano T. Kimura M., Kawana R., Yamamura A. M. A new combined trivalent live measles (AIK-C, strain), mumps (Hoshino strain), and rubella (Takahasi strain) vaccines. Findings in clinical and laboratory studies, Am J. Dis. Child. 144:905–910, 1990.
7. Bluck R., Hoskins J. M., Wegmann A., Just M., Germanier R. Rubini, a new live attenuated mumps vaccine virus strain for human diploid cells.. Dev Biol Stand 65:29–35, 1986.
8. Sassani A., Mirchamasy H. Shafyi A., Ahourai, P., Razavi J. Gholami R. Mohammadi A., Ezzi A., Rahmani M. Fateh G. Paravandi T. Developments of a new live attenuated mumps virus vaccine in human diploid cells. Biologicals 19:203–211, 1991.
9. Smorodintsev A. A., Kiyachko N. S., Nasibov N. M. , Schickina E. S. Experience with live mumps virus vaccine in against Viral and Rickettsial Disease of Man. Washington, D.C., Pan American health Organization, 1967.
10. Fescharek R., Quast U., Maass G., Merkle W., Schwartz S. Measles-mumps vaccination in the FRG An empirical analysis after 14 years of use. II. Tolerability and analysis of spontaneously reported side effects, Vaccine 8:446–456, 1990.
11. Nalin D. Mumps vaccine complications: Which strain? Lancet 2:1396, 1989
12. Cizman M., Mozetic M. Radescek-Rakar R. Pleterski Rigier D., Susec-Michieli Asceptic meningitis after vaccination against measles and mumps. Pediatr. Infect Dis J 8:302–308, 1989.
13. Nalin D. Evaluating mumps vaccine. Lancet 339:305.
14. Ehrengut W., Zastrow K. Komplikationen "nach" Mumpsschutzimpfungen in der Bundersrepublik Deutschland. Monatsschr Kinderheilkd 137:398–402, 1989.
15. Sugiura A. Yamada A. Aseptic meningitis as a complication of mumps vaccination. Pediatr Infect Dis J 10:209–213, 1991.
16. Fujinaga T., Youichi M., Hiroshi T. Takayoshi K. A prefecture-wide survey of mumps meningitis associated with measles, mumps and rubella vaccine. Pediatr Infect Dis J 10:204–209, 1991.
17. Furesz J. Contreras G. Vaccine-related mumps meningitis—Canada. Can Dis Wklyl Rep 16:253–254, 1990.
18. Miller E., Goldacre M., Pugh S., Colville A., Farrington P. Flower A., Nash J., MacFarlane L., Tettmar R. Risk of asceptic meningitis after measles, mumps and rubella vaccine in UK children. Lancet 341: 979–982, 1993.
19. Nokes D. J., Anderson R. M. Vaccine safety versus vaccine efficacy in mass immunisation programmes. Lancet 338: 1309–1312, 1991.
20. Peltola H. Mumps vaccination and meningitis. Lancet 341: 994–995, 1993.
21. Elliot G. D., M. A. Afzal, S. J. Martin and B. K. Rima, 1989, Nucleotide sequence of the matrix, fusion and putative SH protein genes of mumps virus and their deduced amino acid sequences. Virus Res. 61–75.
22. Turner, P. C., Forsey, T. and Minor, P. D (1991) Comparison of the nucleotide sequence of the SH gene and flanking regions of mumps vaccine (Urabe strain) grown on different substrates and isolated from vaccines. J. Gen. Virol. 72: 435–437.
23. Afzal, M. A., A. R. Pickford P. J. Yates, T. Forsey and P. D. Minor, 1994. Matrix protein gene sequence of vaccine and vaccine-associated strains of mumps virus. J. Gen Virology 75, 1169–1172.
24. Tyler, K. L. and B. N. fields. 1990. Pathogenesis of viral infections. in *Fields Virology Vol.* 1, 2nd Edition, pages 989–1012. (B. N. Fields and D. Knipe Eds.) Raven Press, New York.
25. Brown E. G. 1990 Increased virulence of a mouse-adapted variant of influenza A/FM/1/47 virus is controlled by mutations in genome segmens 4, 5, 7, and 8. Journal of Virology 64:4523–4533.
26. Smeenk C. A., and E. G. Brown, 1992. The influenza virus variant A/FM/1/47-MA possesses single amino acid replacements in the hemagglutinin, controlling virulence, and in the matrix protein, controlling virulence as well as growth. Journal of Virology 68:530–534.
27. Brown E. G., C. F. Dimock, and K. Hannah, 1992. Interference is controlled by segment 2 and possibly 28. Snyder, M. H., R. F. Betts, D. DeBorde, E. L. Tierney, M. L. Clements, D. Herrington, S. D. Sears, R. Dolin, H. F. Maassab and B. R. Murphy. Four viral genes independently contribute to attenuation of live influenza A/Ann Arbour/6/60 (H2N2) cold-adapted reassortant virus vaccines. J. Virol. 62:488–495, 1988.
29. Kovamees J., R. Rydbeck, C. L. Orvell and E. Norrby. 1990. Hemagglutinin-neuraminidase (NS) amino acid alterations in neutralization escape mutants of Kilhani mumps virus. Virus Res. 17, 119–130.
30. Orvell, C. 1984. The reaction of monoclonal antibodies with structural proteins of mumps virus. J. Immunol. 132:2622–2629.
31. Afzal, M. A., A. R. Pickford, T. Forsey, A. B. Heath and P. D. Minor, 1993 Three Jeryl Lynn vaccine strains of mumps virus is a mixture of two distinct isolates. J. Gen. Virology, 74:917–920.
32. Brown, E. G., Furesz, J., Dimock, K., Yarosh, W. and Contreras, G. (1991) Nucleotide sequence analysis of Urabe mumps vaccine strain that caused meningitis in vaccine recipients. Vaccine 9: 840–842.
33. Sanger, F., Nicklen, S. and Coulson, A. R. (1977) DNA sequencing with chain-terminating inhibitors. Proc. Natl. Acad. Sci. USA 71: 5463–5467.
34. Winship, P. R. (1989) An improved method for directly sequencing PCR amplified material using dimethyl sulphoxide. Nuc. Acids Res. 17: 1266.
35. Sambrook, J., Fritsch, E. F. and Maniatis, T. (1989) Molecular Cloning a Laboratory Manual. Second Edition. Cold Spring Harbor Laboratory Press, New York.
36. Yamanishi, K., Takahashi, M., Ueda, S., Minekawa, Y., Ogino, T., Suzuki, N. and Okuno, Y. (1973) Studies on live mumps virus vaccine. V. Development of a new mumps vaccine "AM9" by plaque cloning. Biken J. 16: 161–166.
37. Buynak, E. B. and Hilleman, M. R. (1966) Live attenuated mumps virus vaccine. I. Vaccine development. Proc. Soc. Exp. Biol. Med. 123: 768–775.
38. Yamanishi, K., Takahashi, M., Kurimura, T., Ueda, S., Minekawa, Y., Ogino, T., Suzuki, N., Baba, K. and Okuno, Y. (1970) Studies on live mumps virus vaccine. III. Evaluation of newly developed mumps virus vaccine. Biken J. 13: 157–161.
39. Kovamees, J., Norrby, E. and Elango, N. (1989) Complete nucleotide sequence of the hemagglutinin-neuraminidase (HN)m RNA of mumps virus and comparison of paramyxovirus HN proteins. Virus Res. 12: 87–96.

What we claim is:

1. A substantially homogeneous and pure Urabe mumps virus strain Am9 characterized by having a codon encoding glutamic acid at amino acid position 335 of the haemagglutinin-neuraminidase (HN) protein and devoid of any other Urabe mumps virus strain not having the characterizing codon.

2. The mumps virus strain of claim 1 wherein said codon is GAA.

3. A mumps vaccine comprising the virus of claim 1.

4. The mumps vaccine of claim 3 further comprising at least one additional non-mumps pathogen.

5. The mumps vaccine of claim 4 wherein said at least one additional non-mumps pathogen comprises at least one of attenuated or killed measles virus, attenuated or killed rubella virus, or subunits of said measles or rubella viruses.

6. A method of immunizing a host against disease caused by mumps virus infection, which comprises administering an effective amount of a vaccine of claim 3.

7. A method of producing a mumps vaccine, comprising:
administering the virus of claim 1 to a test host to determine dosage and frequency of administration of a vaccine containing the same to elicit a protective immune response in said test animal, and
formulating the vaccine in a form suitable for administration to a treated host in accordance with said determined dosage and frequency of administration.

8. A mumps virus strain having the specific identifying characteristics of that deposited with ATCC under Accession No. VR 2521.

* * * * *